United States Patent [19]
Kochersperger et al.

[11] Patent Number: 5,656,034
[45] Date of Patent: Aug. 12, 1997

[54] HIGH-PRESSURE MICRO-VOLUME SYRINGE PUMP

[76] Inventors: Michael L. Kochersperger, 4227 Skymont Dr., Belmont, Calif. 94002; Reid B. Kowallis, 2875 Canyon Rd., Burlingame, Calif. 94010; Andrew A. Pham, 236 Bonita La., Foster City, Calif. 94404

[21] Appl. No.: 414,663

[22] Filed: Mar. 31, 1995

[51] Int. Cl.$^6$ .......................... A61M 37/00; B01D 15/08
[52] U.S. Cl. .......................... 604/155; 604/121; 604/151; 210/656; 210/659
[58] Field of Search .................. 604/28, 65, 67, 604/121, 151, 152, 154, 155, 218, 245, 250

[56] References Cited

U.S. PATENT DOCUMENTS

| | | |
|---|---|---|
| 4,347,131 | 8/1982 | Brownlee. |
| 4,767,406 | 8/1988 | Wadham et al.. |
| 4,804,290 | 2/1989 | Balsells .................. 403/326 |
| 4,882,063 | 11/1989 | Allington et al. ........... 210/101 X |
| 5,006,112 | 4/1991 | Metzner. |
| 5,071,562 | 12/1991 | Allington et al. ........... 210/101 X |
| 5,080,785 | 1/1992 | Allington et al. ........... 210/101 X |
| 5,219,099 | 6/1993 | Spence. |

OTHER PUBLICATIONS

Van Vlack, L.H. Elements of Materials Science and Engineering, Fourth Edition, Chapters 8 and 9, Addison–Wesley (1980).
Krstulovic et al. Reversed–Phase High–Performance Liquid Chromatography, John Wiley & Sons, New York (1983).
Model 172 Series HPLC Separation System Installation Manual, Part No. 0054–0012, Applied Biosystems Division of the Perkin–Elmer Corporation, Foster City, CA (May 1992).
Moritz et al. Journal of Chromatography 599: 119–130 (1992) Application of capillary reversed–phase high–performance liquid chromatography to high–sensitivity protein sequence analysis.
INSTAC/LIF Technical Handbook, pp. 66–69, The Lee Company, Los Angeles, CA (1987).
Product Bulletin: Turcite Internally Lubricatred Materials, W.S. Shamban & Co., Newbury Park, CA.
Material Specification Compound 1043, American Variseal, Broomfield, CO.
Material Specification Compound 1103, American Variseal, Broomfield, CO.
Machinery's Handbook, 24th Edition, pp. 1604–1607, Industrial Press, Inc., N.Y. (1992).
Richerson Modern Ceramic Engineering, pp. 438–489, Marcel Dekker, N.Y. (1992).

*Primary Examiner*—Sam Rimell
*Assistant Examiner*—Robert V. Racunas
*Attorney, Agent, or Firm*—Paul D. Grossman

[57] ABSTRACT

A syringe pump particularly adapted for delivery of small volumes at a high pressure in an accurate and reproducible manner. The syringe pump includes a frame, a motor attached to the frame, and a lead screw drivably connected to the motor. A cover seal is mounted to the front end of the lead screw, the cover seal having grooves formed therein to facilitate mounting and demounting of the cover seal. The pump further includes a cylindrical barrel within which the cover seal reciprocates, the barrel being made of a ceramic material, wherein the barrel is fixedly attached to the frame at the front end and floatably mounted to the frame at the back end. A barrel head is mounted to the front end of the barrel for closing off that end of the barrel, the barrel head including an outlet port for allowing fluid to enter and exit the barrel. In addition, the present invention includes a multi-syringe gradient syringe pump, a liquid chromatography system, a cover seal, and a mixer for mixing multiple flow streams.

25 Claims, 12 Drawing Sheets

HIGH-PRESSURE MICRO-VOLUME SYRINGE PUMP

BACKGROUND

This invention relates to syringe pumps. More specifically, this invention describes a high-pressure micro-volume syringe pump particularly suited to for analytical separations.

An important trend in modern analytical chemistry has been the move towards separation techniques capable of accommodating small sample volumes, i.e., sample volumes in the range of 1 to 10 µl. This trend is particularly strong in the area of analytical biotechnology where samples are frequently derived from scarce natural isolates or from valuable recombinant products. Typical analytical biotechnology applications include chromatographic separations used as part of protein sequencing operations, amino acid analysis, protein/peptide mapping, quality control of pharmaceutical products, and the like.

To avoid dilution of the sample and thereby maintain the delectability of the separated components, the scale of the separation columns, e.g., chromatographic columns, has been reduced to match the scale of the samples, such micro-scale columns having internal diameters as small as 50 µm. An added benefit of scaling down the separation equipment is the reduced volume of working fluid required, e.g., chromatographic solvents and/or eluants, leading to reduced costs for acquiring and disposing of such materials, particularly in the case of exotic and/or highly toxic materials.

Micro-scale separations place a particular burden on the pumps used to deliver the working fluid to the separation column. The performance characteristics of typical HPLC pumps is not adequate to satisfy the exacting demands of such micro-column separations-where an error of ±1 µl might be undetectable in a HPLC application running at a flow rate of 2 ml/min, that same error could lead to unacceptably large errors in a micro-column application running at a flow rate of less than 10 µl/min.

Syringe pumps are well suited to the demands of micro-column chromatographic separations. Syringe pumps have several advantages over reciprocating pumps when used for micro-scale analytical separations, e.g., liquid chromatography, super critical fluid chromatography, and the like, including (i) essentially pulse-free fluid flow and (ii) highly reproducible and accurate volumetric fluid delivery.

However, currently available syringe pumps have a number of important shortcomings. In particular, existing syringe pumps are not able to deliver low solvent flow rates at high pressure with the requisite accuracy and precision desirable for analytical separations. Furthermore, existing syringe pumps transmit a high level of mechanical vibrations to the working fluid, thereby interfering with detection of the separated sample components. Another drawback of existing syringe pumps is that wear on moving sealing surfaces is such that parts including such sealing surfaces frequently wear out, leading to poor run-to-run reproducibility and necessitating frequent pump disassembly and replacement of the worn parts.

When used in a multiple-pump gradient mode, because of the shortcomings noted above, existing syringe pumps are unable to produce reproducible gradients, particularly at very low solvent flow rates and at high pressure. To achieve low flow rates in a multiple-pump gradient mode, existing syringe pumps require the use of a solvent splitter which serves to direct a portion of the outflow from the pump to a waste stream rather to the separation column, e.g., Moritz et at., Journal of Chromatography 599:119–130 (1992). Such splitting techniques introduce large errors in the solvent delivery profile due to changes in the solvent density and viscosity as the composition of the solvent is changed throughout the gradient. In addition, existing systems require mixers which have relatively large internal volumes, introduce significant noise into the flow stream, and release particulates into the flow stream as a result of wear of the moving parts.

SUMMARY

An object of our invention is to provide a syringe pump capable of delivering very low flow rates, i.e., less than 10 µl/min, at high pressures, i.e., greater than 700 psi, in a highly precise and accurate manner.

A further object of our invention is to provide a syringe pump having a mechanism which minimizes mechanical vibrations, thereby minimizing the mechanical noise reaching any attached detector.

Another object of our invention is to provide a syringe pump having a design which minimizes wear on any moving sealing surfaces, thereby increasing the lifetime of components including such moving sealing surfaces.

Yet another object of our invention is to provide a multiple-syringe gradient syringe pump capable of providing a solvent composition gradient which is highly reproducible, i.e., having a relative standard deviation of less than 0.25% when operating at low flow rates, i.e., less than 10 µl/min, and at high pressures, i.e., greater than 700 psi.

A further object of our invention is to provide a multiple-syringe gradient syringe pump capable of operating at very low flow rates, e.g., less than 10 µl/min, without splitting the solvent stream.

Another object of our invention is to provide a mixer for mixing multiple fluid streams which has a small internal volume, thoroughly mixes the fluid streams, introduces a minimum amount of noise into the flow stream, and does not release particulates into the flow stream as a result of wear.

The foregoing and other objects of the present invention are achieved by a high pressure micro-volume syringe pump which includes, in one aspect, a frame for mounting the components of the pump, and a motor attached to the frame. The pump further includes a lead screw which is drivably connected to the motor, and a cover seal, the cover seal being mounted to the lead screw, the cover seal having slits formed therein to facilitate mounting and demoting of the cover seal. The cover seal undergoes reciprocal movement inside a cylindrical barrel, the barrel axis being coaxially aligned with the lead screw axis. The barrel is made of a ceramic material and is fixedly attached to the frame at one end and floatably mounted to the frame at the other end. Finally, a barrel head is mounted to one end of the barrel for closing off that end, the barrel head including an outlet/inlet port for allowing a working fluid to enter and exit the barrel.

In another aspect, the invention includes a mutli-syringe gradient syringe pump including a plurality of high-pressure micro-volume syringe pumps as described above and a mixer for mixing the fluids exiting each of the pumps.

In yet another aspect, the invention includes a liquid chromatography system including one or more high-pressure micro-volume syringe pumps as described above, a chromatography column connected to the outlet/inlet of the syringe pumps, an injector, located between and in fluid communication with the syringe pump and the chromatography column, and a detector in communication with the outlet/inlet of the chromatography column such that material leaving the chromatography column is detectable by the detector.

In another aspect, the invention includes a cover seal for use in a high-pressure micro-volume syringe pump, the cover seal being adapted to mount onto a cover seal mounting member. The cover seal includes a cylindrical body in which a cavity is formed, the body being made of high molecular weight polyethylene. The outside surface of the body has grooves formed therein such that when the outside surface of the body is not constrained, as the cover seal is pushed onto the mounting member, the radial dimension of the cavity can increase, thereby facilitating the placement of the cover seal onto the mounting member and the removal of the cover seal from the mounting member.

In another aspect, the invention includes a mixer for mixing multiple fluid streams. The mixer includes an enclosed bowl having an inside bottom surface which is a bearing surface, the bearing surface being made from a ceramic material. The bowl further includes an inlet port and an outlet port for providing fluid communication between the bowl and the surroundings. A puck adapted to undergo rotational motion is located inside the bowl. The puck has helical groves formed on its outside surface and a puck magnet located in its interior. The mixer also includes a motor and an external magnet connected to the motor such that the external magnet undergoes rotational motion. The external magnet is located such that it is in magnetic communication with the puck magnet so that rotation of the external magnet causes rotation of the puck.

These and other objects, features, and advantages of the present invention will become better understood with reference to the following description, drawings, and appended claims.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Figure 1:
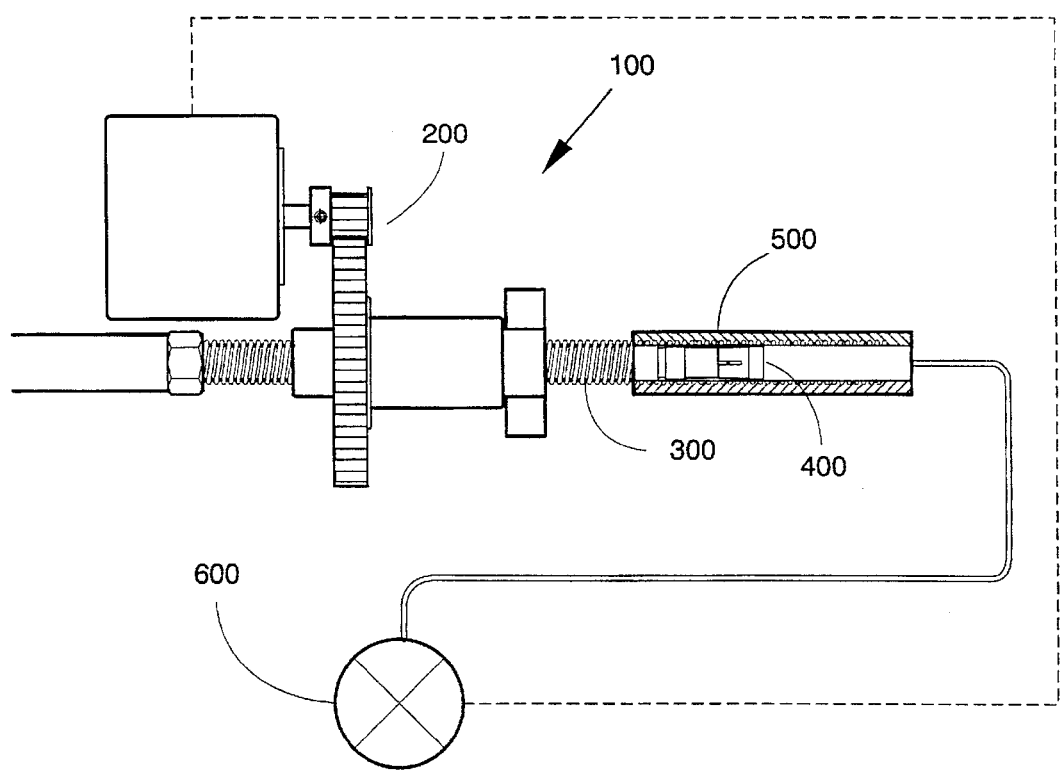
FIG. 1 shows a schematic representation of the high-pressure micro-volume syringe pump of the present invention.

Referring now to the drawings, where like numbers indicate like elements, FIG. 1 shows a schematic representation of the syringe pump of the present invention (100) comprising a drive assembly (200) for providing rotational mechanical power to the pump, a linear drive train (300) for converting the rotational mechanical power into linear motion, a barrel assembly (500) for defining a high-pressure containment volume, and a cover seal (400) for providing a movable sealing surface for varying the internal volume of the barrel assembly. The syringe pump also includes a valve assembly (600) for controlling the flow of material leaving the pump during pumping and/or entering the pump during filling, and a controller (655) for monitoring and controlling various aspects of the pump.

1. Drive Assembly

Figure 2:
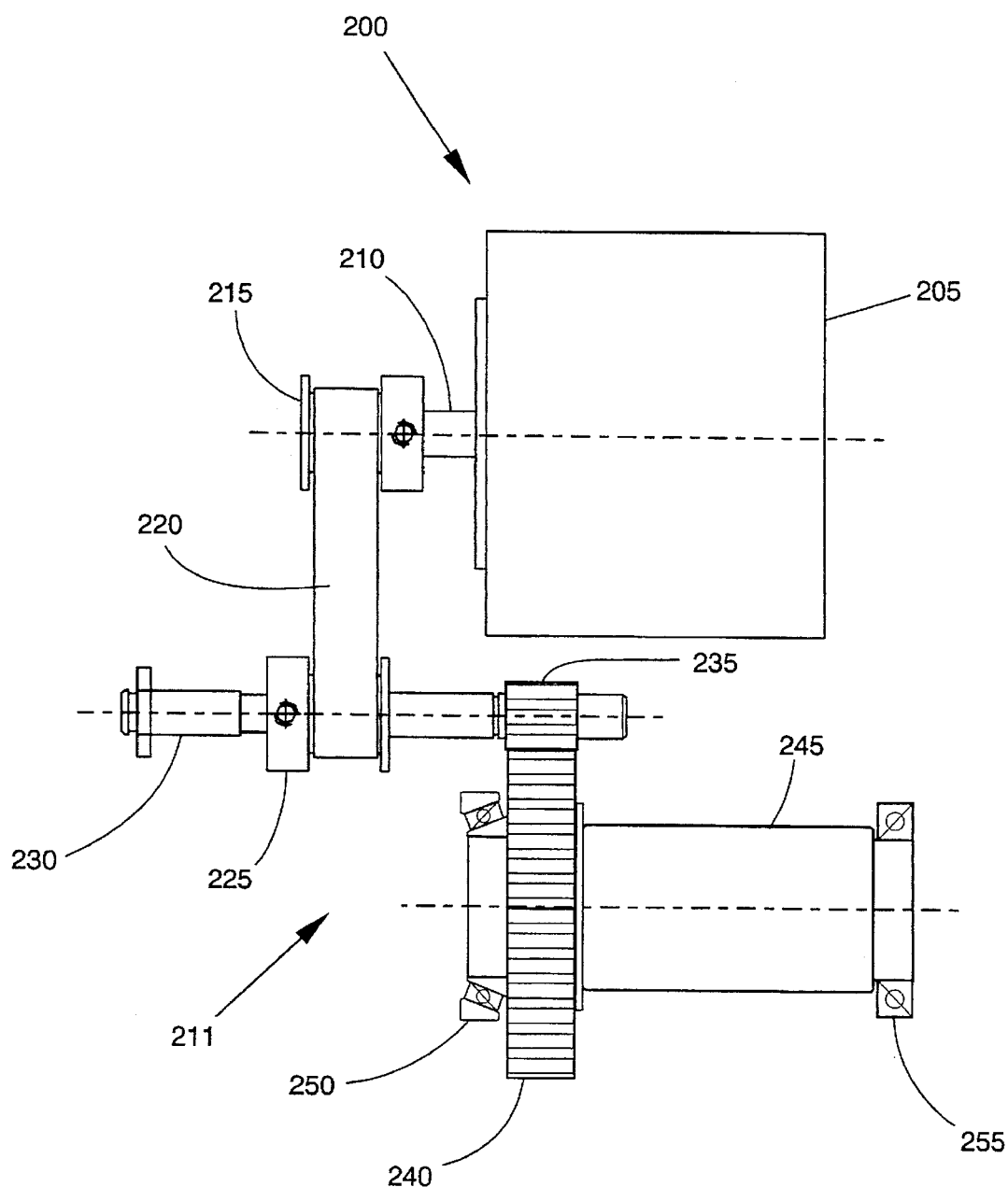
FIG. 2 shows a preferred drive assembly of the high-pressure micro-volume syringe pump of the present invention.

FIG. 2 shows a detailed drawing of a preferred drive assembly of the syringe pump of the present invention. Generally, the preferred drive assembly (200) includes a means for moving a lead screw, preferably a motor (205), drivably connected to a nut (245) by a power transmission (211), the rotation of the nut transmitting energy to the linear drive train.

The motor should be capable of being controlled by an electronic controller and provide an output which can be delivered in small increments of rotation, e.g., increments on the order of 0.03° /step. The small increments of rotation coupled with a small inner diameter of the barrel assembly, allow for very precise delivery of liquid at low flow rates. Preferably, the motor is a stepper motor, i.e., a motor in which the extent of rotation is controllable in discrete steps. More preferably, the motor is a stepper motor capable of micro-stepping operation, i.e., stepping in increments of 10,000 or more steps per revolution. Additionally, the preferred motor should be able to produce a static torque of at least 60 oz-in. An exemplary motor is the Model 23H-530A stepper motor available from American Precision Industries, Inc., Rapidsyn Division, Oceanside, Calif.

Preferably, the power transmission (211) drivably connecting the motor (205) and the nut (245) should (i) decrease the effective step size of the motor's output rotation, where as used herein, the "effective step size" is defined as the ratio of the angular rotation of the nut to the angular rotation of the motor; (ii) increase the torque produced by the motor and transmitted to the nut; and (iii) provide mechanical dampening to reduce the amount of vibration transmitted from the motor (205) to the nut (245). A preferred power transmission includes a first timing pulley (215) mounted to a motor drive shaft (210), a second timing pulley (225) mounted to a jack shaft (230), and a timing belt (220) drivably connecting the first timing pulley (215) and the second timing pulley (225). Rotational motion is transmitted from the jack shaft (230) to a drive gear (240) through a pinion gear (235) mounted on the jack shaft (230). The drive gear (240) is mounted on the nut (245), thereby transmitting its rotational motion to the nut.

The optimal amount of gear reduction between the motor (205) and the nut (245) is based on a compromise between minimizing the effective step size of the motor output and minimizing the time required to fill the pump. Thus, as the amount of gear reduction is increased, the effective step size of the motor is decreased, but the time required to refill the pump is increased. In the pump of the present invention, a preferred gear reduction is 5:1, such gear reduction being accomplished by making the diameter of the drive gear five times that of the pinion gear while making the diameters of the first and second timing pulleys equal.

The rotational motion of the preferred drive assembly described above is translated into linear motion of a lead screw (303, FIG. 3A) through the nut (245), the nut having a nut rotational axis (246) and the lead screw having a lead screw translational axis (304). Threads formed on the inside bore of the nut drivably engage the lead screw (303) such that rotation of the nut (245) by the drive gear (240) imparts a linear translation to the lead screw (303) along a lead screw axis (304). Preferably, the nut (245) is made from a material which is both (i) compliant and (ii) has a low coefficient of friction. The compliance of the material serves to dampen mechanical noise in the system while the low coefficient of friction allows the nut to operate without any external lubrication. By eliminating external lubrication, the pump is easier to maintain, and more importantly, the opportunity for contamination of the working fluids is greatly reduced. Preferred materials for forming the nut include oil-filled bronze, Rulon®, Delrin®, and the like. More preferably the nut is made from Teflon®-filled Delrin®, e.g., Turcite-X®, e.g., Product Bulletin, Turcite Internally Lubricated Materials, W. S. Shamban & Co., Newbury Park, Calif. (1989), reference herein incorporated by reference.

The nut is mounted onto a forward bearing (250) and a rear bearing (255) such that the nut is free to rotate but is prevented from undergoing translational motion. One or more preload springs (330) serve to urge the nut against the rear bearing (255) thereby taking up the mechanical tolerances of the system. In addition, the bearings serve to maintain alignment of the nut with respect to the barrel assembly (500) such that the lead screw (303) is held coaxially with respect to the barrel assembly (500).

2. Linear Drive Train

Figure 3B:
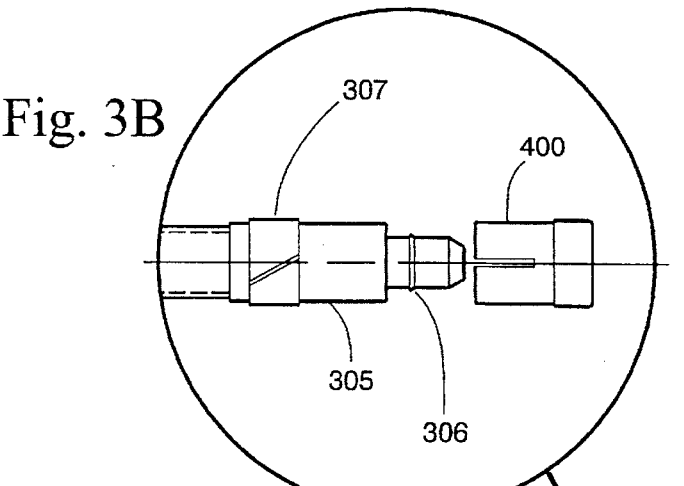
FIGS. 3A and 3B show a preferred linear drive train of the high-pressure micro-volume syringe pump of the present invention.
Figure 3A:
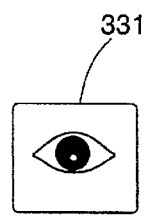
Figure 3A:
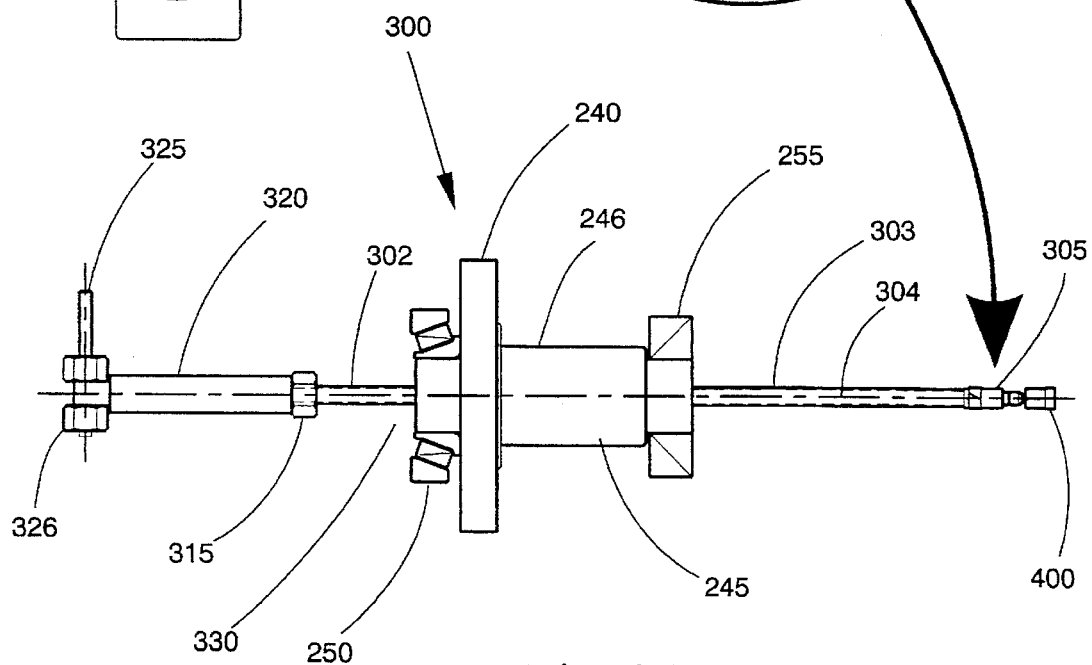
Figure 3C:
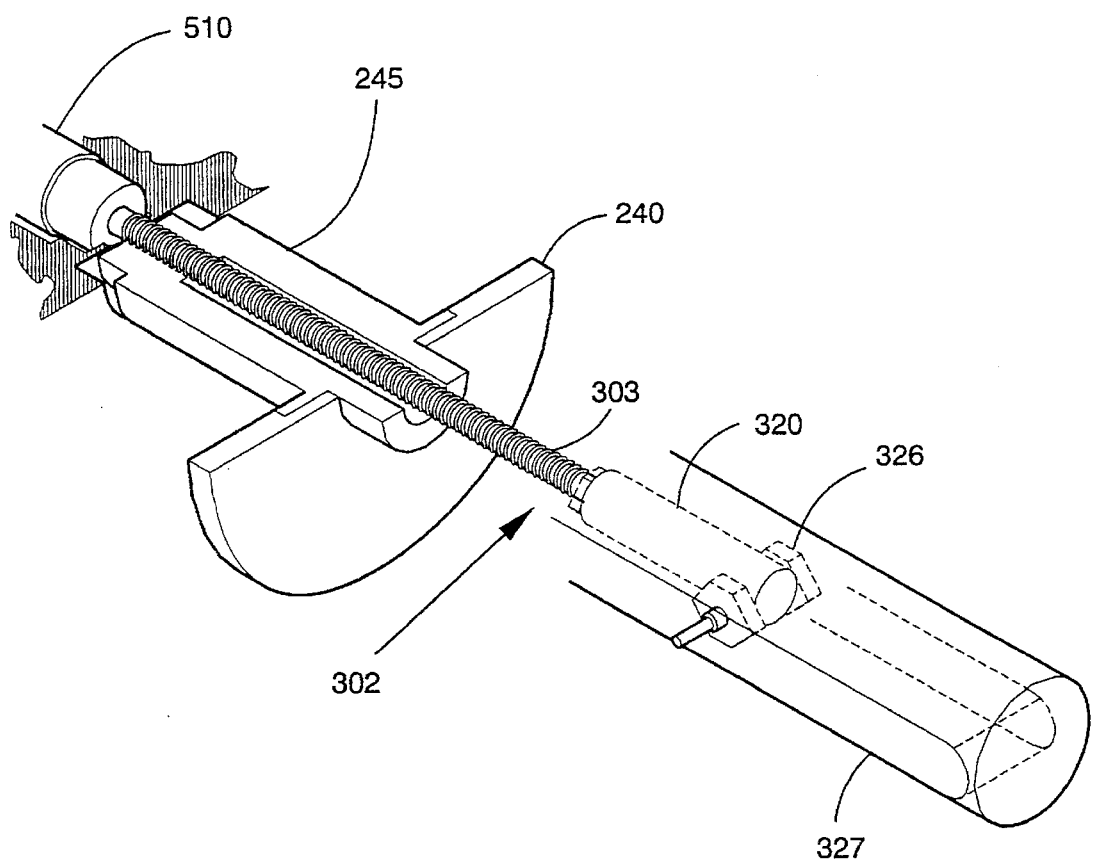
FIG. 3C shows an isometric view of the rear portion of a preferred linear drive train of the high-pressure micro-volume syringe pump of the present invention.

FIGS. 3A–C show a detailed view of a preferred linear drive train of the present invention including the lead screw (303), the lead screw having a front end (301) and a back end (302), a cover seal mounting member (305), a cover seal (400), and a lead screw follower (320). Preferably, the thread form of the lead screw is chosen such that unnecessary wear and stress on the nut is minimized. More preferably, the lead screw thread profile is an Acme thread profile, e.g., Machinery's Handbook, 24th Edition, pages 1604–1607, Industrial Press, Inc., N.Y. (1992), the reference herein incorporated by reference. Even more preferably, the lead screw thread profile is an Acme thread profile having a 3/16 inch nominal major diameter and a lead resulting in 20 turns per inch, and is and made from stainless steel.

Preferably, the back end (302) of the lead screw includes a constraining means for preventing rotation of the lead screw while allowing translation of the lead screw. In the preferred embodiment shown in FIGS. 3A and 3B, the back end of the lead screw is attached to a follower (320) having a pair guide blocks (326) attached thereto. The follower (320) and the guide blocks (326) are located within a follower guide (327), the follower guide having a rectangular internal cross section. In operation, as rotational force is applied to the lead screw (300), the guide blocks (326) engage the follower guide (327), thereby preventing the lead screw from rotating.

In one preferred embodiment, a position sensor flag (325) is located at the end of the follower (320) at which the jam nuts (326) are mounted. The position sensor flag serves to indicate to a lead screw position sensor (331) when the lead screw (303) has reached the end of its allowed extent of travel. The position sensor (331) can be an optical sensor, an electrical sensor, or any other like sensor capable of indicating the presence or absence of the lead screw (300) at a defined location. More preferably, the sensor is an optical sensor.

Mounted on the from end (301) of the lead screw (303) is a cover seal mounting member (305). The cover seal mounting member serves to mount the cover seal (400) to the lead screw (303) in a detachable manner. Preferably, the cover seal mounting member includes a retaining barb (306) and a guide bushing (307). The retaining barb (306) serves to hold the cover seal (400) onto the mount in a removable manner, while the guide bushing (307) serves to reduce the radial loads on the cover seal and to assist in maintaining the proper alignment between the linear drive train (300) and the barrel assembly (500). The guide bushing (307) is mounted in a guide bushing mounting grove (340) such that the guide bushing (307) is flush with the outside surface of the cover seal mounting member. Preferably the guide bushing (307) is made of an elastomeric material which (i) is wear resistant, (ii) which will not scratch the inside surface of the barrel, and (iii) is chemically inert to solvents typically used in chromatography, e.g., polyetheretherketone PEEK, e.g., Material Specification for Compound 1043 from American Variseal, Broomfield, Colo., the reference herein incorporated by reference.

3. Cover seal

Figure 4A:
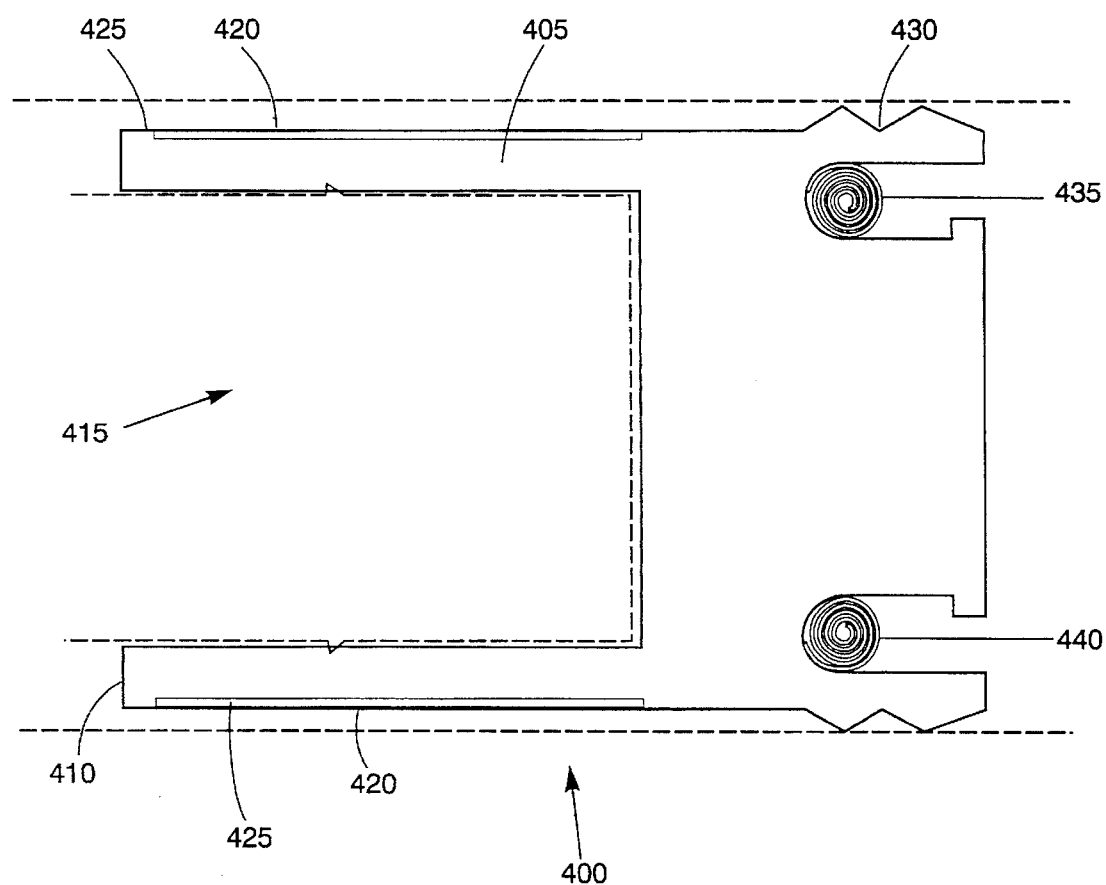
FIG. 4A shows a preferred cover seal of the high-pressure micro-volume syringe pump of the present invention.
Figure 4B:
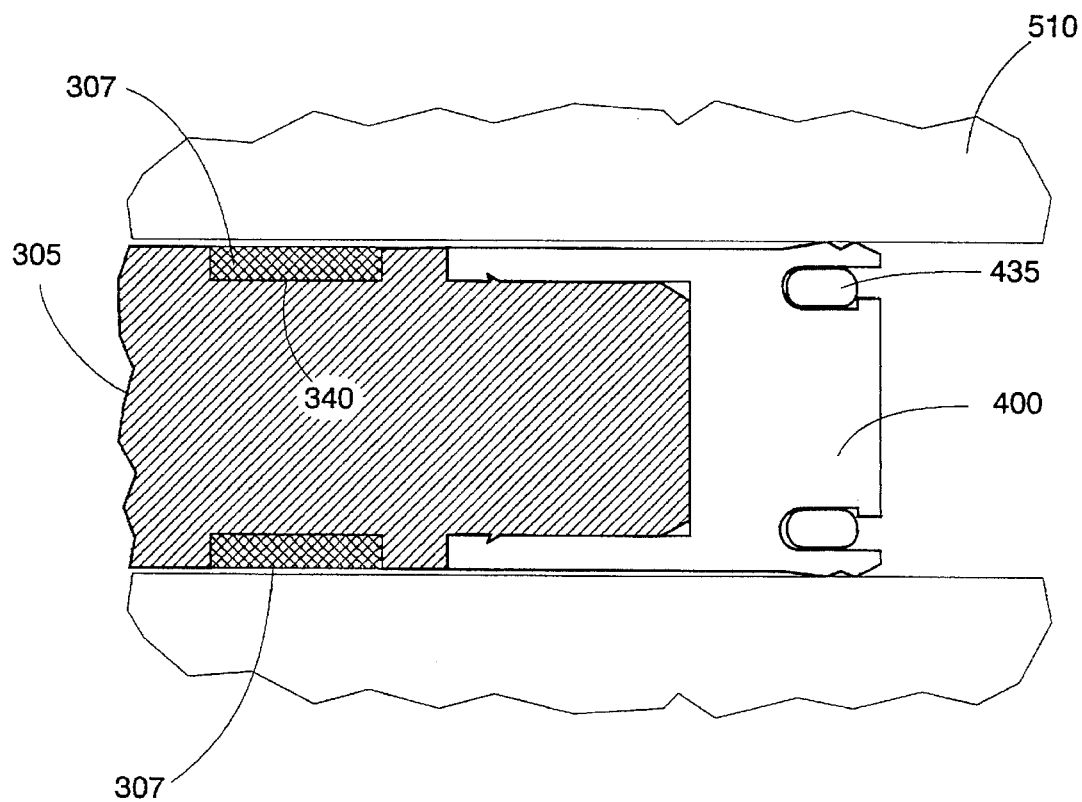
FIG. 4B shows the preferred cover seal of FIG. 4A mounted on a cover seal mounting member.

FIGS. 4A and 4B show an expanded view of a preferred cover seal (400) of the present invention. The preferred cover seal includes a body (405) with a cavity formed therein (415), the cavity designed to fit over the cover seal mounting member (305). At the front of the perimeter of the cover seal are a plurality of sealing ridges (430) for providing superior sealing between the barrel assembly (500) and the cover seal. Formed in the front of the cover seal is a mounting groove (440) for containing an energizer (435) for providing force in a radially outward direction for the purpose of maintaining a seal between the cover seal (400) and the barrel assembly (500). Preferably, the energizer is an O-ring formed of an elastomeric material, a round-strip loading spring, a U/V circular loading spring, a helical spring, or any other like means for providing radial force. More preferably, the energizer is a helical spring. The energizer (435) serves to force the sealing ridges (430) in a radially outward direction to provide positive sealing between the sealing ridges and the inside wall of the barrel assembly (500) when the seal is not under pressure.

In an important aspect of the cover seal of the present invention (400), the outside surface (420) of the body (405) of the cover seal has grooves (425) formed therein, the grooves running in an axial direction. The grooves (425) serve to facilitate the expansion of the internal diameter of the cavity (415) as the cover seal is mounted to or removed from the cover seal mounting member (305). However, when the cover seal is located inside the barrel assembly (500), the cover seal is firmly held onto the cover seal mounting member (305) because the walls of the barrel assembly prevent expansion of the cavity. This preferred design facilitates manual replacement of worn cover seals.

Preferably, the cover seal is made from a resilient material which withstands wear due to friction, has a minimum of stick-slip when in contact with ceramic surfaces, and does not cold flow. Preferred materials include Teflon®, Kel-F®, Tercel®, and the like. More preferably, the preferred cover seal is made from ultra high molecular weight polyethylene, e.g., Compound 1103 available from the America Veriseal Company, Broomfield, Colo., Material Specification for Compound 1103 herein incorporated by reference.

4. Barrel Assembly

Figure 5A:
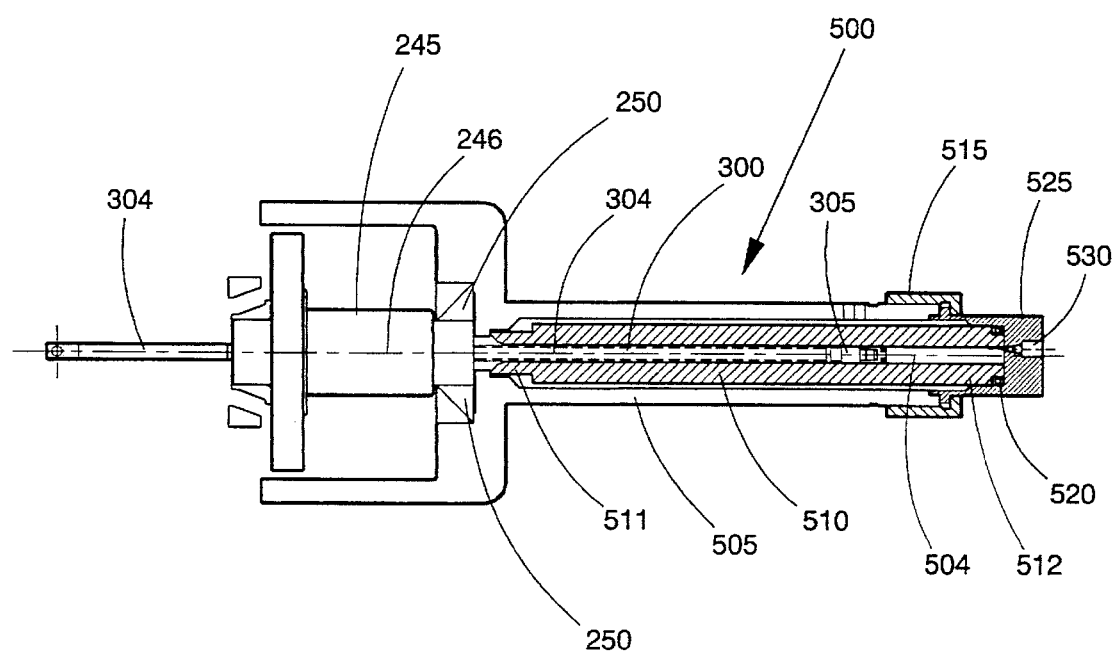
FIG. 5A shows a preferred barrel assembly of the high-pressure micro-volume syringe pump of the present invention.
Figure 5B:
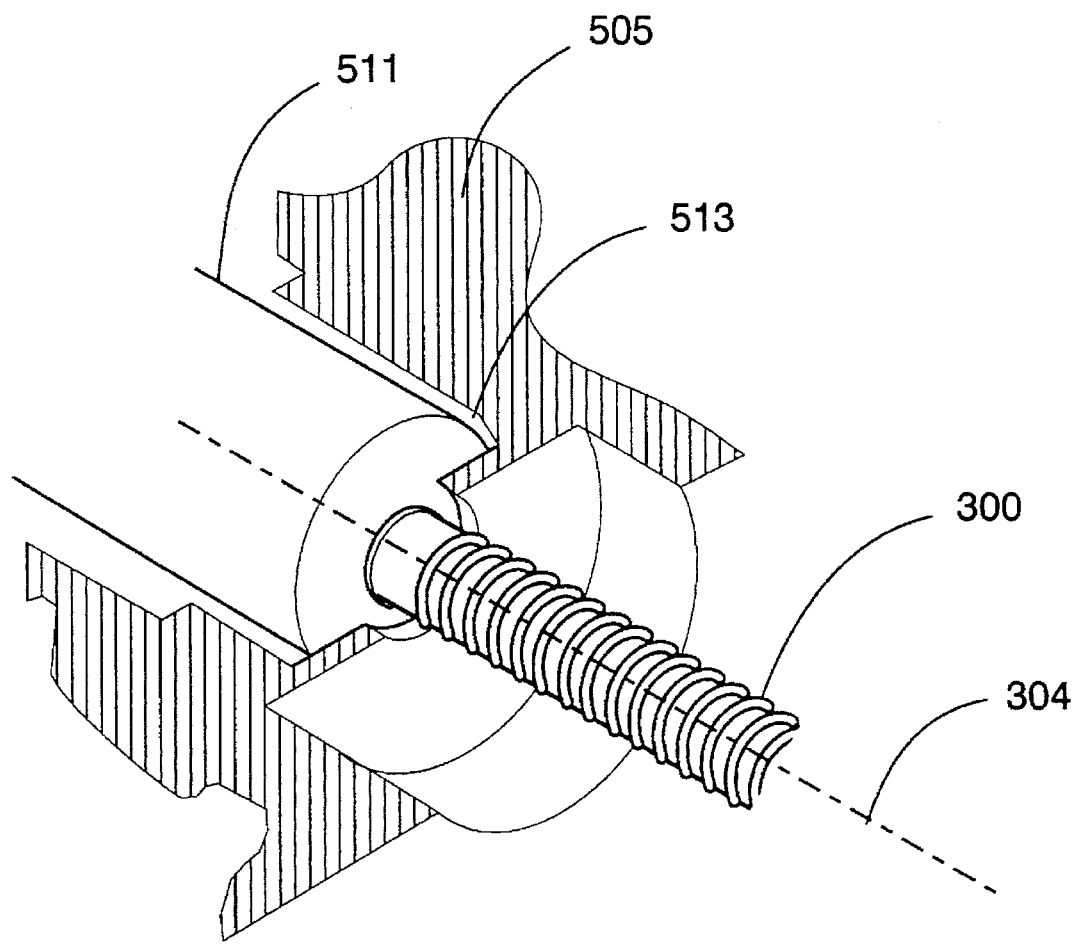
FIG. 5B shows an expanded view of the floating end of a preferred barrel assembly of the present invention.

A preferred barrel assembly (500) is shown in FIGS. 5A and 5B. A barrel (510) is contained in a barrel housing (505) with one end capped by a cylinder head (520) and the other end open to receive the linear drive train (300), the barrel having a floating end (511) and a fixed end (512). A cylinder head (525) is mounted to a barrel housing (505), preferably using a retaining nut (515) which is threaded onto the exterior of the barrel housing (505). The cylinder head (525) has an inlet/outlet port (530) formed therein to facilitate the fluid connection of the pump to associated tubing preferably, a high pressure seal is formed between the cylinder head (525) and the barrel housing (505) by a head seal (520).

In an important feature of the barrel assembly (500), one end of the barrel is "floating", i.e., the floating end (511), while the opposite end (512) is pivotally mounted to the frame. By allowing the floating end to float, the barrel (510) can adjust to compensate for any nonuniformity in the rotation of the lead screw (300), nut (245), or front bearings (250). Ideally, the nut rotational axis (246) and the lead screw translational axis (304) are coaxial. However, because of imperfections in the fabrication of the nut (245) and the lead screw (300), these axis are not perfectly coaxial. Therefore, the rotation of the nut (245) can cause a side loading on the lead screw (300) which in turn can cause a side load on the cover seal (400). This side load on the cover seal can lead to excessive wear of the cover seal (400) and/or leaking of fluid past the cover seal into the mechanism of the pump, leading to corrosion of the pump reduced precision of the pump.

FIG. 5B shows the floating end of the barrel (511) and how it is floatably mounted to the barrel housing (505). By allowing an appropriate clearance (513) between the barrel (510) and the barrel housing (505), side loads transmitted from the nut to the lead screw (300) will result in a radial movement of the barrel with respect to the barrel housing rather than an increased side load on the cover seal (400).

Another important feature of the preferred barrel assembly (500) is that the barrel (510) is made of a ceramic material, where, as used herein, the term "ceramic" refers to materials which are compounds of metallic and nonmetallic elements, e.g., $Al_2O_3$, Cu—Zn, Cu—Sn, Al—Cu, Al—Mg, Fe—O, and the like, e.g., Van Vlack, Elements of Materials Science and Engineering Fourth Edition, Chapter 9 (Addison-Wesley, Menlo Park, 1980) said reference incorporated herein by reference. Ceramic materials are preferred because of (i) their smooth surface, which reduces the wear on the cover seal and improves the sealing between the cover seal and the barrel; (ii) their extreme chemical stability; and (iii) their resistance to scratching. Preferably the ceramic material is 99.8% $Al_2O_3$. More preferably, the ceramic materials used in the present invention are made by a process which uses no flow enhancing agents to facilitate processing, e.g., elastomeric additives or emulsifiers. By not using such additives, the resulting ceramic product has smaller grains, resulting a material which is harder and smoother. More preferably, the ceramic materials used in the present inventions are formed by the isostatic pressing process, e.g., Richerson, Modern Ceramic Engineering, pages 438-489, Marcel Dekker, N.Y. (1992), the reference hereby incorporated by reference.

Preferably, the inside diameter of the barrel (510) and all associated elements of the barrel assembly and the linear drive train are chosen to accommodate micro-volume pumping applications. Preferably, the inside diameter of the barrel is less than 0.25 inches. By having a small diameter barrel, any errors in the linear translation of the linear drive train (300) will result in only small errors in the volume of fluid pumped.

5. Single Pump Valve Assembly

In a preferred embodiment of the syringe pump of the present invention, the syringe pump includes a valve assembly (600) for directing flow into or out of the syringe pump. A detailed flow diagram of a preferred valve assembly is shown in FIG. 6, the valve assembly being capable of directing flow out of the syringe pump to waste or to an application, e.g., a liquid chromatography column, supercritical chromatography column, or the like, or directing flow from a solvent reservoir into the syringe pump for filling the pump.

Figure 6:
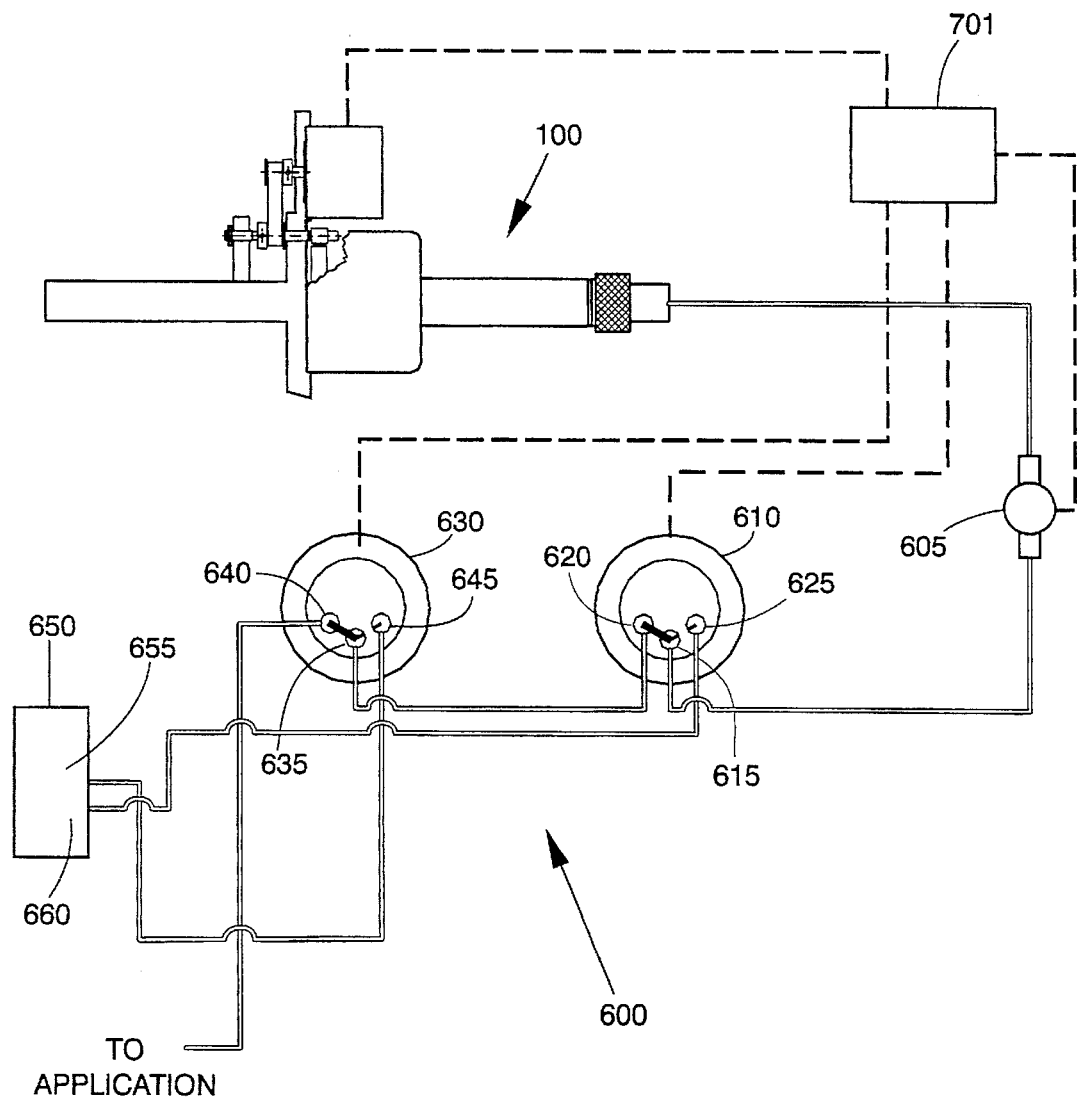
FIG. 6 shows a flow diagram of a preferred valve assembly of the high-pressure micro-volume syringe pump of the present invention.

The preferred valve assembly shown in FIG. 6 includes first (610) and second (630) 3-way valves, a pressure transducer (605), a flow manifold (650), and a controller (701). Preferably, the first 3-way valve (610) includes a common port (615), a first selectable port (620), and a second selectable port (625), where the common port (615) is alternatively connected to the first selectable port (620) or the second selectable port (625). In the preferred arrangement shown in FIG. 6, the common port (615) is connected to the output of the pump, the first selectable port (620) is connected to the second valve (630), and the second selectable port (625) is connected to the manifold (650). An exemplary preferred valve is the Rheodyne Model 7030S valve (Rheodyne, Inc., Cotatti, Calif.).

Similarly, the second 3-way valve (630) includes a common port (635), a first selectable port (640), and a second selectable port (645), where the common port (635) is alternatively connected to the first selectable port (640) or the second selectable port (645). In the preferred arrangement shown in FIG. 6, the common port (635) is connected to the first selectable port of the first valve (620), the first selectable port (640) is connected to the application, and the second selectable port (645) is connected to the manifold (650).

Preferably, at least one of the valve ports is connected to the flow manifold (650) having a waste position (655) and a solvent position (660).

A pressure transducer (605) is included in the preferred valve assembly (600) to warn of an overpressure and/or underpressure condition in the flow path caused by clogging and/or valve malfunction.

In a more preferred embodiment the controller (701) is used to control inputs and outputs for monitoring and directing the operation of the pump and associated systems. Typical inputs would include inputs from (i) a user interface, (ii) the pressure transducer, (iii) an external start signal, (iv) valve position sensors, and (v) the head screw position sensor. Typical outputs from the controller would include (i) outputs to the motor for controlling the motor speed, (ii)

outputs to a user interface, (iii) outputs to valve-position serves, and (iv) outputs to a RS232-type serial interface. A typical controller would be any suitable PC-based controller, e.g., the Turbochrome System from Perkin-Elmer Corporation, Norwalk, Conn.

To fill the barrel (510) using the preferred valve assembly (600) shown in FIG. 6, the first valve (610) is positioned such that the common port (615) is connected to the second selectable port (625), thereby eliminating the second valve (630) from the flow path and connecting the barrel (500) to the solvent port (660) of the manifold (650). Thus, when a negative pressure is generated in the syringe pump by retracting the cover seal, solvent will flow from the solvent port (660) of the manifold (650) into the barrel (510) of the pump.

To pump the contents of the syringe pump (100) to waste, the first valve (610) is positioned such that the common port (615) is connected to the first selectable port (620), thereby connecting the first valve (610) to the second valve (630), and the second valve (630) is positioned such that the common port (635) is connected to the second selectable port (645). Alternatively, to pump the fluid contents of the barrel (510) to an application, the first valve (610) is positioned such that the common port (615) is connected to the first selectable port (620), thereby connecting the first valve (610) to the second valve (630), and the second valve (630) is positioned such that the common port (635) is connected to the first selectable port (640).

6. Multiple Pump Valve Assembly

Figure 7:
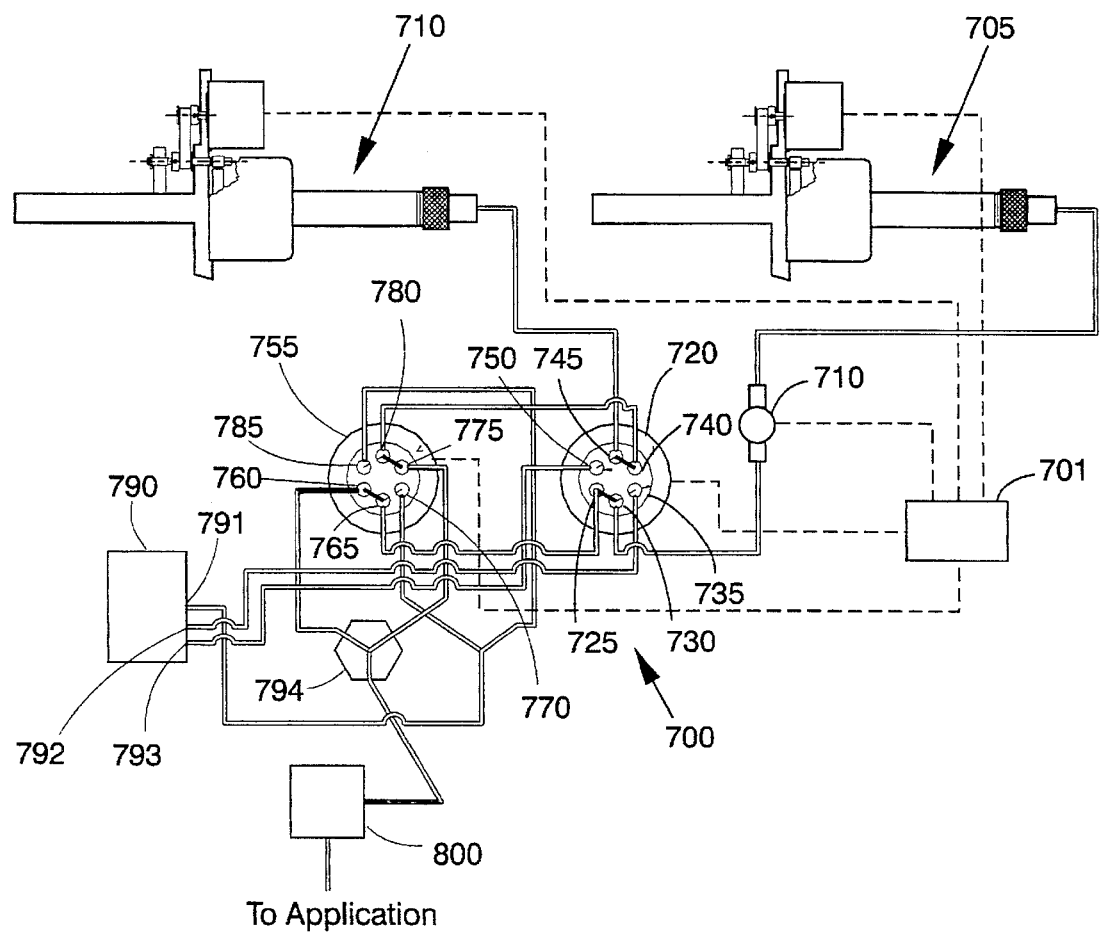
FIG. 7 shows a preferred flow diagram of a mutli-syringe gradient syringe pump system of the present invention.

In an alternative embodiment, the valve assembly of the present invention is arranged such that multiple syringe pumps can be used in combination to create solvent composition gradients. FIG. 7 shows such a multiple pump valve assembly having two syringe pumps. Obviously it would be possible to use three or more pumps to provide solvent gradients based on the same principles.

Generally, the preferred multiple pump valve assembly (700) shown in FIG. 7 includes first (720) and second (755) double 3-way valves, a pressure transducer (715), a flow manifold (790), a controller (701), a mixing tee (794) and a solvent mixer (800).

Preferably, the first double 3-way valve (720) includes a first group of three ports consisting of a first selectable port (725), a second selectable port (735), and a first common port (730), where the first common port (730) is alternatively connected to the first selectable port (725) or the second selectable port (735), and a second group of three ports consisting of a third selectable port (740), a fourth selectable port (750), and a second common port (745), where the second common port (745) is alternatively connected to the third selectable port (740) or the fourth selectable port (750). In the preferred arrangement shown in FIG. 7, the ports of the first group of ports of the first double 3-way valve (720) are connected as follows: the first common port (730) is connected to the output of the first syringe pump (705), the first selectable port (725) is connected to the second double 3-way valve (755), and the second selectable port (735) is connected to the manifold (650) at a solvent "A" position. Similarly, the ports of the second group of ports of the first double 3-way valve (720) are connected as follows: the second common port (745) is connected to the output of the second syringe pump (710), the third selectable port (740) is connected to the second double 3-way valve (755), and the fourth selectable port (750) is connected to the manifold (650) at a solvent "B" position.

In a manner analogous to the first double 3-way valve (720), the second double 3-way valve (755) includes a first group of three ports consisting of a first selectable port (760), a second selectable port (770), and a first common port (765), where the first common port (765) is alternatively connected to the first selectable port (760) or the second selectable port (770), and a second group of three ports consisting of a third selectable port (775), a fourth selectable port (785), and a second common port (780), where the second common port (780) is alternatively connected to the third selectable port (775) or the fourth selectable port (785). In the preferred arrangement shown in FIG. 7, the ports of the first group of ports of the second double 3-way valve (755) are connected as follows: the first common port (765) is connected to the first double 3-way valve (720), the first selectable port (760) is connected to the mixer (800) through the mixing tee (794), and the second selectable port (770) is connected to the manifold (790) at a waste position (791). Similarly, the ports of the second group of ports of the second double 3-way valve (755) are connected as follows: the second common port (780) is connected to the first double 3-way valve (720), the third selectable port (775) is connected to the mixer (800) through the mixing tee (794), and the fourth selectable port (785) is connected to the manifold (790) at the waste position.

Any suitable mixer may be used in the present invention. Preferably the mixer (i) has a small internal volume, i.e., less than two times the fluid volume being pumped through the system in a minute, (ii) thoroughly mixes multiple flow streams, (iii) introduces a minimum mount of noise, i.e., high frequency pressure fluctuations, into the flow stream, and (iv) does not introduce particulate debris into the flow stream as a result of disintegration of moving components.

An important aspect of the present invention is the discovery of a mixer which is particularly well suited to micro-scale, high pressure applications where multiple fluid streams must be thoroughly mixed, e.g., gradient liquid chromatography.

Figures 8A, 8B, 8C:
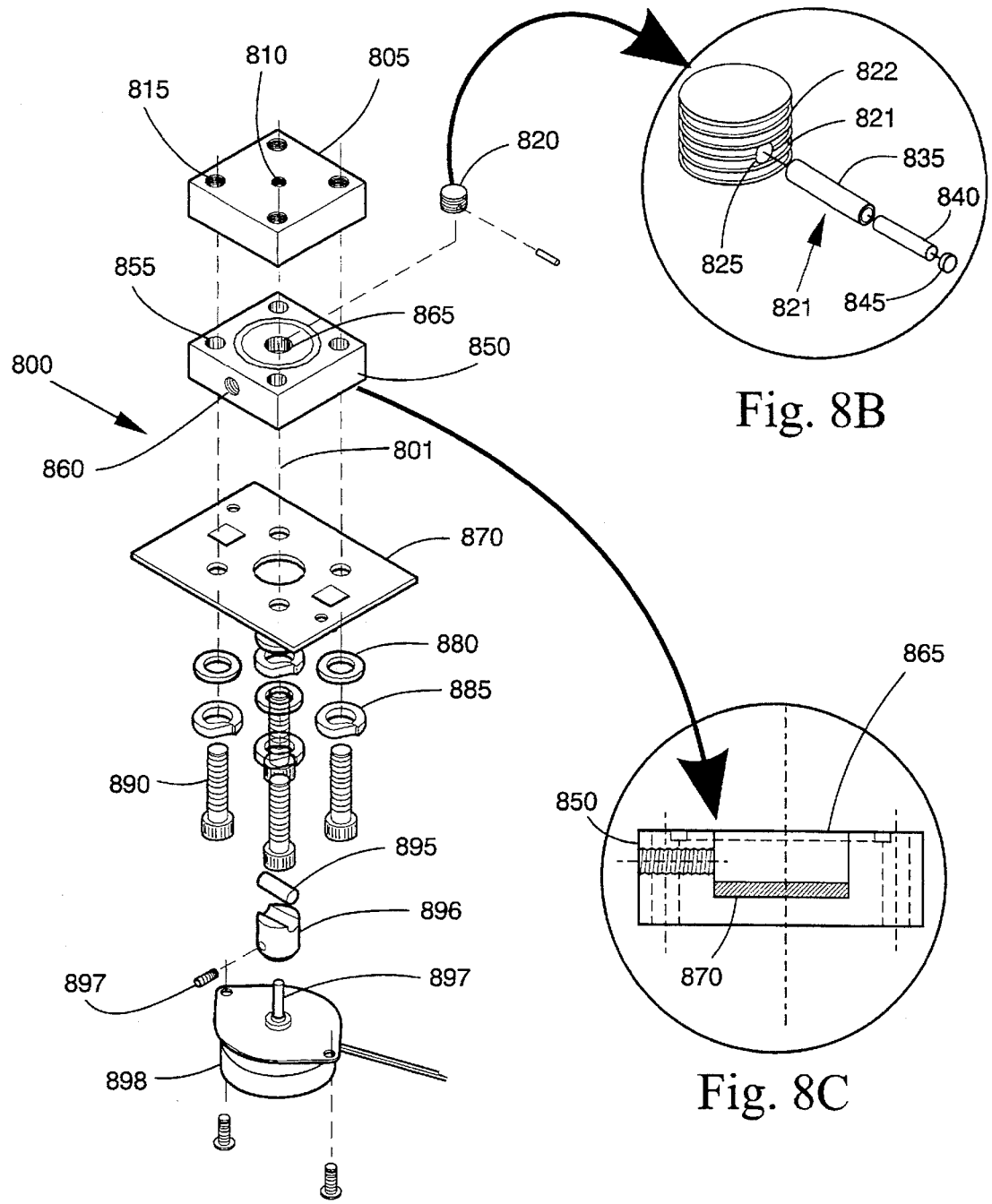
FIGS. 8A–C shows an exploded view of a preferred mixer of the present invention.

With reference to FIGS. 8A–C, generally, the preferred mixer of the present invention includes a body (850) having a bowl (865) formed therein, a puck (820) including a puck magnet (840), and driver magnet (895) which is mounted external to the bowel but in magnetic communication with the puck magnet (840) and which is rotatably driven by a motor (898). Therefore, the rotating driver magnet (895) serves to cause rotation of the puck (820), thereby causing agitation of the fluid located in the bowel (865).

The body (850) has a fluid inlet port (860) for providing fluid communication between the bowl (865) of the mixer (800) and other elements of the pumping system. The bottom surface of the bowl is a bearing surface (870) on which the puck (820) rotates. Preferably, this bearing surface (870) is formed from a hard material, i.e., hard with respect to the puck material, which is resistant to deterioration under the wear of the spinning puck (820), thereby minimizing the opportunity for particulate debris to be introduced into the fluid stream. More preferably, the bearing surface is made from a ceramic material. The top surface of the bowl is formed by a mixer cap (805) which is sealably attached to the body (850) of the mixer, where the mixer cap has a fluid outlet port (810) formed therein to provide fluid communication between the bowl (865) an other elements of the system.

The size and composition of the puck magnet (840) should be such that the magnetic force between the puck magnet (840) and the driver magnet (895) is sufficient to overcome the frictional drag between the puck and the bowl and the frictional drag between the puck and the agitated fluid stream while providing a rotational velocity of the puck (820) sufficient to fully agitate the fluid stream. The puck magnet may be formed from any material having a magnetic dipole, e.g., iron and the like, however, because of the size limitations on the magnet imposed by the size of the puck (820), a strongly magnetic material is preferred; a particularly preferred magnetic material being a samarium-cobalt alloy.

In a preferred arrangement the puck magnet (840) is made part of a puck magnet assembly (830), said assembly including a canister (835), the puck magnet (840), and a canister cap (845). When fully assembled, the puck magnet (840) is sealed inside the canister (835) by welding the canister cap (845) in place. Preferably, the welding is laser welding which produces a small heat affected zone. The canister material should be particularly resistant to corrosion, e.g., type 316 L stainless steel, to minimize contamination of the fluid stream. By enclosing the puck magnet (840) inside the corrosion resistant canister (835), the fluid stream is protected from contamination from the puck magnet.

Preferably, the outside surface of the puck (822) has a helical grove (821) formed therein. As the puck spins, the helical grove serves to cause circulation of the fluid resulting in extreme agitation of the fluid. To enhance agitation and to reduce the dead volume of the mixer, the diameter of the puck (820) should be such that only a small distance separates the outside surface of the puck (822) and the inside surface of the bowl (865); preferably this distance is less than 1 mm. In a preferred embodiment, the puck includes a magnet mounting hole (825) for firmly holding the puck magnet (840) or magnet assembly (830) such that the rotational force applied to the puck magnet (840) by the rotating driver magnet (845) is efficiently transmitted to the puck itself.

Preferably, the driver magnet (895) is mounted to the motor (898) by a magnet holder (896), said holder being securely attached to a motor drive shaft (899).

In the preferred embodiment shown in FIGS. 8A-C, the mixer is assembled as follows: the mixer cap (805), the body (850) and a motor mounting plate (875) are held together by a plurality of bolts (890) or other like fastening means, and the motor (898) is securely fastened to the motor mounting plate (875), wherein the motor drive shaft (899), the driver magnet (895), the bowl (865) all lie substantially on a mixer rotational axis (801).

Clearly, other suitable mixers may be used with the general pumping system of the present invention. Possible alternative mixers include static mixers, e.g., INSTAC/LIF Technical Handbook, pages 66–69, The Lee Company, Los Angeles, Calif. (1987)

In a preferred arrangement, a mixing tee (794) is placed upstream of the mixer (800) to "premix" the converging flow streams.

In operation, to form a solvent gradient with the preferred dual pump valve assembly (700) shown in FIG. 7, flow from both the first syringe pump (705) and the second syringe pump (710) are mixed, where each pump is filled with a different solvent composition. The gradient is achieved by varying the flow rates of each pump such that the combined volumetric flow form the pumps is held substantially constant, while the composition is changed by varying the flow rates of each pump. To achieve flow from both pumps simultaneously, the solvent from the first syringe pump (705) passes through open valve ports (730), (725), (765), and (760), while the solvent from the second syringe pump (710) passes through open valve ports (745), (740), (780), and (775), then on to the mixer (800) where the flows originating from both of the syringe pumps are mixed then transmitted to the application.

7. Liquid Chromatography System:

In a particularly preferred application, the syringe pump of the present invention may be used in a liquid chromatography system (900), more preferably in a micro-volume chromatography system.

Figure 9:
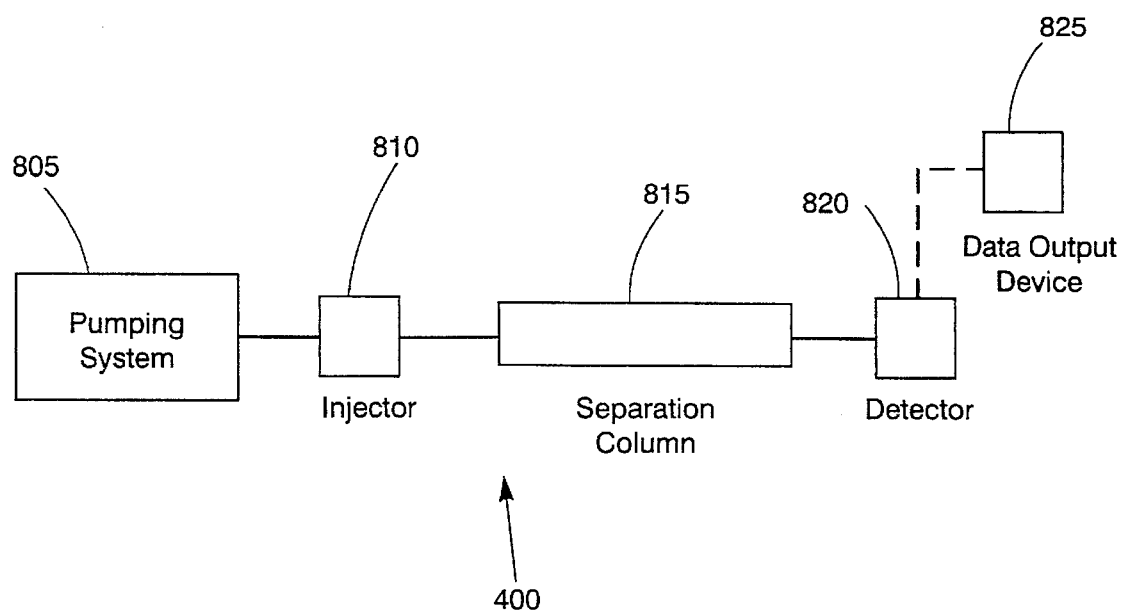
FIG. 9 shows a schematic diagram of a preferred chromatography system of the present invention.

The preferred chromatography system shown in FIG. 9 includes a pumping system (905) where the pumping system comprises one or more syringe pumps as described herein, a sample injector (910) for injecting sample onto a chromatography column (915), a detector (920) and a data output device (925). A complete discussion of how liquid chromatography systems are assembled is given elsewhere, e.g., Krstulovic et al., Reversed-Phase High-performance Liquid Chromatography, Chapter 3, John Wiley & Sons, New York (1982); and Model 172 Series HPLC Separation System Installation Manual, Part Number 0054–0012, Applied Biosystems Division of the Perkin-Elmer Corporation, Foster City, Calif. (May 1992).

Although only a few embodiments have been described in detail above, those having ordinary skill in the arts of chromatography or pump design will clearly understand that many modifications are possible in the preferred embodiment without departing from the teachings thereof. All such modifications are intended to be encompassed within the following claims.

We claim:

1. A high pressure micro-volume syringe pump for pumping a working fluid comprising:

a frame;

a motor attached to the frame;

a lead screw drivably connected to the motor, said lead screw having a front end and a lead screw translational axis;

a cover seal, the cover seal being mounted to the front end of the lead screw; and a cylindrical barrel within which the lead screw and cover seal undergo reciprocal axial movement, the barrel having a front end, a back end, and a barrel axis, the barrel axis being coaxially aligned with the lead screw axis, the barrel being made of a ceramic material, wherein the barrel is pivotally attached to the frame at the front end and floatably mounted to the frame at the back end.

2. The high pressure syringe pump of claim 1 wherein the coverseal has grooves formed in its outside surface to facilitate mounting and demoting of the cover seal.

3. The high pressure syringe pump of claim 1 further including a barrel head mounted at the front end of the barrel for closing off that end of the barrel, the barrel head including an outlet port for allowing the working fluid to enter and exit the barrel.

4. The high pressure syringe pump of claim 1 further including a constraining means for preventing rotation of the lead screw while allowing translation of the lead screw.

5. The high pressure syringe pump of claim 1 further including a controller.

6. The high pressure syringe pump of claim 1 further including a power transmission drivably interposed between the motor and the lead screw.

7. The high pressure syringe pump of claim 6 wherein the power transmission includes a nut made from Teflon-filled Delrin.

8. The high pressure syringe pump of claim 1 further including a valve assembly in fluid connection with the outlet/inlet port.

9. The high pressure syringe pump of claim 1 wherein the motor is a stepper motor.

10. The high pressure syringe pump of claim 9 wherein the stepper motor is capable of micro-stepping operation.

11. The high pressure syringe pump of claim 1 wherein the lead screw has an Acme thread profile.

12. The high pressure syringe pump of claim 1 wherein the cover seal is made from a resilient material.

13. The high pressure syringe pump of claim 12 wherein the cover seal is made from ultra high molecular weight polyethylene.

14. The high pressure syringe pump of claim 1 wherein the cover seal comprises:

a cylindrical body having a cavity formed therein and formed from high molecular weight polyethylene, the body having an outside surface, the outside surface having grooves formed therein such that when the outside surface of the body is not constrained, as the cover seal is pushed onto a mounting member, the radial dimension of the cavity can increase, thereby facilitating the placement of the cover seal onto the mounting member and the removal of the cover seal from the mounting member; and an energizer mounted in the body to cause the outside surface to be urged in a radially outward direction.

15. A mutli-syringe gradient syringe pump comprising:

a plurality of high-pressure micro-volume syringe pumps for pumping multiple working fluids, each syringe pump comprising:

a frame;

a motor attached to the frame;

a lead screw drivably connected to the motor disposed in a barrel for reciprocal axial movement therein, said lead screw having a front end and a lead screw translational axis;

a cover seal, the cover seal being mounted to the front end of the lead screw; and a cylindrical barrel within which the cover seal undergoes reciprocal movement, the barrel having a front end, a back end, and a barrel axis, the barrel axis being coaxially aligned with the lead screw axis, the barrel being made of a ceramic material, wherein the barrel is pivotally attached to the time at the front end and floatably mounted to the frame at the back end; and a mixer for mixing the working fluids exiting each pump.

16. The mutli-syringe gradient syringe pump of claim 15 further including a controller.

17. The mutli-syringe gradient syringe pump of claim 15 further including a power transmission drivably interposed between the motor and the lead screw.

18. The mutli-syringe gradient syringe pump of claim 15 further including a valve assembly in fluid connection with the outlet/inlet port of each of the high-pressure micro-volume syringe pumps.

19. The mutli-syringe gradient syringe pump of claim 15 wherein the motor is a stepper motor, the stepper motor being capable of micro-stepping operation.

20. The multi-syringe gradient syringe pump of claim 15 wherein the mixer comprises:

an enclosed bowl having an inside bottom surface which is a bearing surface, said bearing surface being made from a ceramic material, and having an inlet port and an outlet port for providing fluid communication between the bowl and the surroundings;

a puck adapted to undergo rotational motion inside the bowl, the puck having helical groves formed on its outside surface and having a puck magnet located in its interior for rotation therewith;

a motor; and an external magnet connected to the motor such that the external magnet undergoes rotational motion, the external magnet being in magnetic communication with the puck magnet.

21. A liquid chromatography system comprising:

one or more high-pressure micro-volume syringe pumps, each syringe pump comprising:

a frame;

a motor attached to the frame;

a lead screw drivably connected to the motor disposed in a barrel for reciprocal axial movement therein, said lead screw having a front end and a lead screw translational axis;

a cover seal, the cover seal being mounted to the front end of the lead screw; and a cylindrical barrel within which the cover seal undergoes reciprocal movement, the barrel having a front end, a back end, and a barrel axis, the barrel axis being coaxially aligned with the lead screw axis, the barrel being made of a ceramic material, wherein the barrel is pivotally attached to the frame at the front end and floatably mounted to the frame at the back end;

a chromatography column in fluid communication with the outlet/inlet of the syringe pumps;

an injector, disposed between and in fluid communication with the syringe pump and the chromatography column, and a detector in communication with the outlet/inlet of the chromatography column such that material leaving the chromatography column is detectable by the detector.

22. A high pressure micro-volume syringe pump for pumping a working fluid comprising:

an elongate barrel mounted on a frame for pivoting about a front end of the barrel, said barrel having a barrel axis and defining a containment volume extending through the barrel;

a lead screw disposed in the barrel for reciprocal axial movement therein, said screw having a front end and a lead screw translational axis;

a cover seal mounted on the front end of the lead screw providing a fluid tight seal with said containment volume; and a means for moving the lead screw axially within the barrel, wherein alignment between the barrel axis and the lead screw translational axis is maintained by pivioting of said barrel about said front end.

23. The high pressure syringe pump of claim 22 wherein the cover seal is made from ultra high molecular weight polyethylene.

24. The high pressure syringe pump of claim 22 wherein the means for moving the lead screw is a stepper motor.

25. The high pressure pump of claim 22 further including a constraining means for preventing rotation of the lead screw while allowing translation of the lead screw.

* * * * *

UNITED STATES PATENT AND TRADEMARK OFFICE
CERTIFICATE OF CORRECTION

PATENT NO. : 5,656,034
DATED      : Aug. 12, 1997
INVENTOR(S) : Michael L. Kochersperger, Reid B. Kowallis, Andrew A. Pham It is certified that error appears in the above-indentified patent and that said Letters Patent is hereby corrected as shown below:

On title page, insert --Assignee: The Perkin-Elmer Corporation, Foster City, Calif.--

Signed and Sealed this

First Day of December, 1998

Attest:

BRUCE LEHMAN

*Attesting Officer*     *Commissioner of Patents and Trademarks*